US009778212B2

(12) United States Patent
Tessema et al.

(10) Patent No.: US 9,778,212 B2
(45) Date of Patent: Oct. 3, 2017

(54) METHOD FOR DETERMINING THE LITHIATION OF LI-ION BATTERY ELECTRODES

(71) Applicant: GM Global Technology Operations LLC, Detroit, MI (US)

(72) Inventors: Misle M. Tessema, Warren, MI (US); Michael P. Balogh, Novi, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 328 days.

(21) Appl. No.: 14/529,828

(22) Filed: Oct. 31, 2014

(65) Prior Publication Data

US 2016/0123906 A1 May 5, 2016

(51) Int. Cl.
*G01N 23/207* (2006.01)
*H01M 10/052* (2010.01)
*H01M 10/42* (2006.01)

(52) U.S. Cl.
CPC ......... *G01N 23/207* (2013.01); *H01M 10/052* (2013.01); *H01M 10/4285* (2013.01)

(58) Field of Classification Search
CPC ............. G01N 23/2055; G01N 23/207; G01N 2223/0566; G01N 2223/601; G01N 2223/605; G01N 2223/633
See application file for complete search history.

(56) References Cited

U.S. PATENT DOCUMENTS

2014/0356718 A1* 12/2014 Ito ......................... H01M 4/505 429/223
2017/0065591 A1* 3/2017 Masjedizadeh .... A61K 31/5395

FOREIGN PATENT DOCUMENTS

JP WO 2013/115390 A1 * 8/2013 ............ H01M 4/505

OTHER PUBLICATIONS

Balasubramanian et al., "In situ X-ray diffraction and X-ray absorption studies of high-rate lithium-ion batteries", Journal of Power Sources, vol. 92, (2001), pp. 1-8.*

* cited by examiner

*Primary Examiner* — Glen Kao
*Assistant Examiner* — Chih-Cheng Kao
(74) *Attorney, Agent, or Firm* — Brooks Kushman P.C.

(57) ABSTRACT

A method for determining an amount of lithium in a lithium-ion battery electrode sample includes a step of determining powder X-ray diffraction peaks of the lithium-ion battery electrode sample. The powder X-ray diffraction peaks of the lithium-ion battery electrode sample are compared with a set of lithium-containing samples having pre-determined lithium concentrations to determine the amount of lithium in the lithium-ion battery electrode sample.

16 Claims, 8 Drawing Sheets

X-ray
32
a
30
b
30
34

METHOD FOR DETERMINING THE LITHIATION OF LI-ION BATTERY ELECTRODES

TECHNICAL FIELD

The present invention is related to methods for determining the composition of electrodes in lithium-ion batteries.

BACKGROUND

Large capacity rechargeable batteries are currently being investigated for use in electric vehicles. The ultimate feasibility of electric vehicles depends on significantly reducing the associated costs. Reduction in the costs of battery assemblies is particularly important.

Lithium-ion batteries are an important type of battery technology. Most battery assemblies, including lithium-ion battery assemblies, include a plurality of individual electrochemical cells. Typically, such electrochemical cells include an anode and a cathode. Typically, the anode includes a metal sheet or foil (usually copper metal) over-coated with a graphitic layer. Similarly, the cathode usually includes a metal sheet or foil (usually aluminum metal) over-coated with a lithium-containing layer. Finally, electrochemical cells include an electrolyte which is interposed between the anode and the cathode. Terminals allow the generated electricity to be used in an external circuit. Electrochemical cells produce electricity via an electrochemical reaction.

The increasing demand for improvements in lithium-ion batteries necessitates a complete understanding of the material in such cells as well as their changing compositions and performance overtime. Moreover, it is desired that such analytic techniques be inexpensive and easy to perform.

Accordingly, there is a need for improved techniques for evaluating compositional and functional changes in lithium-ion batteries.

SUMMARY

The present invention solves one or more problems of the prior art by providing in at least one embodiment, a method for determining an amount of lithium in a lithium-ion battery electrode sample. The method includes a step of determining powder X-ray diffraction peaks of the lithium-ion battery electrode sample. The powder X-ray diffraction peaks of the lithium-ion battery electrode sample are compared with a set of lithium-containing samples having pre-determined lithium concentrations to determine the amount of lithium in the lithium-ion battery electrode sample. Advantageously, the method provides an inexpensive and rapid determination of formulation and compositional information for lithium-ion battery electrodes. Such information is required for quality validation, failure analysis, competitive assessment and cost analysis

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Figure 1:
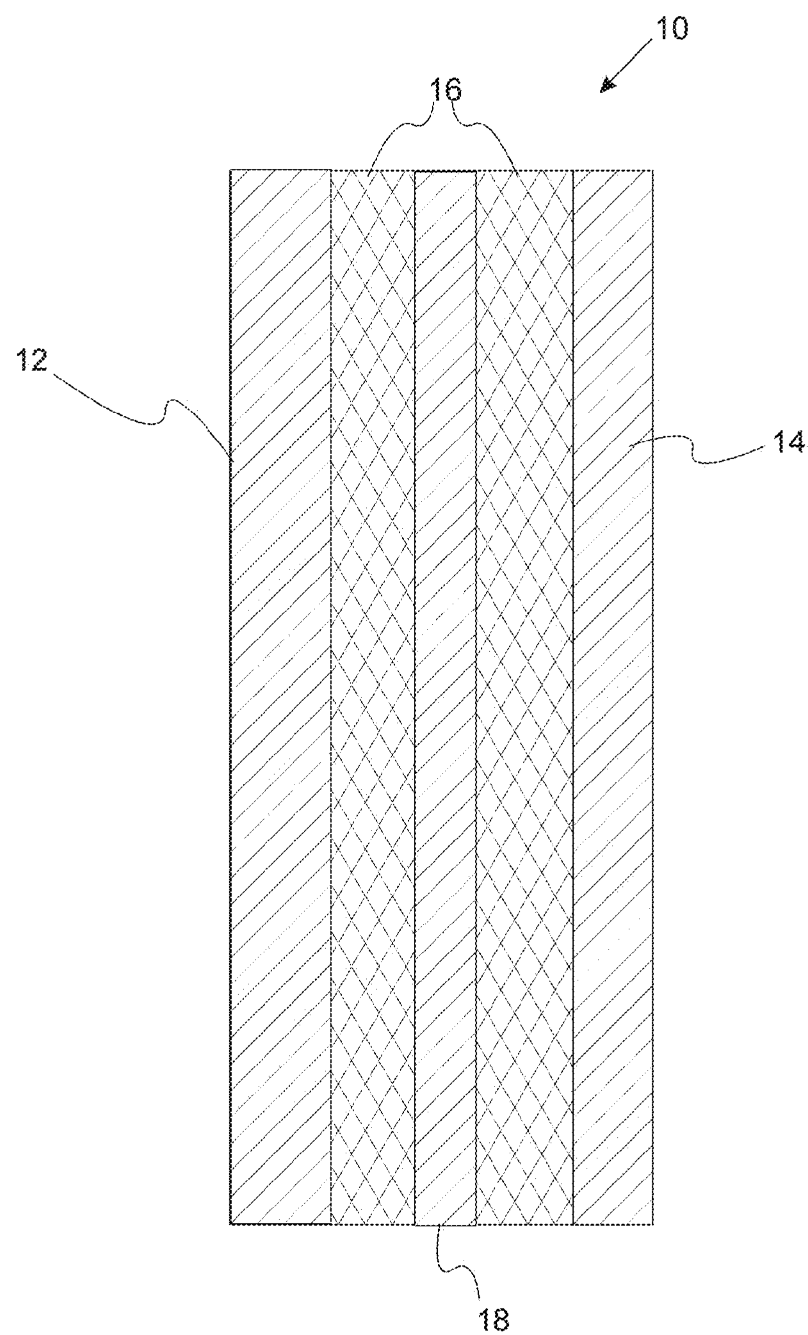
FIG. 1 provides a schematic cross section of a lithium-ion battery assembly.

With reference to FIG. 1, a schematic cross section of a lithium-ion battery assembly incorporating an embodiment of a fibrous sheet is provided. Battery 10 includes anode 12, cathode 14, and electrolyte 16. Typically, anode 12 is made from carbon (e.g., graphite) while cathode 14 is made of a metal oxide (e.g., lithium nickel cobalt oxide). The electrolyte usually includes a lithium salt in an organic solvent.

Separator 18 is interposed between anode 12 and cathode 14 thereby minimizing electrical shorts between the two electrodes while allowing passages of ions such as lithium ($Li^+$).

Figure 2:
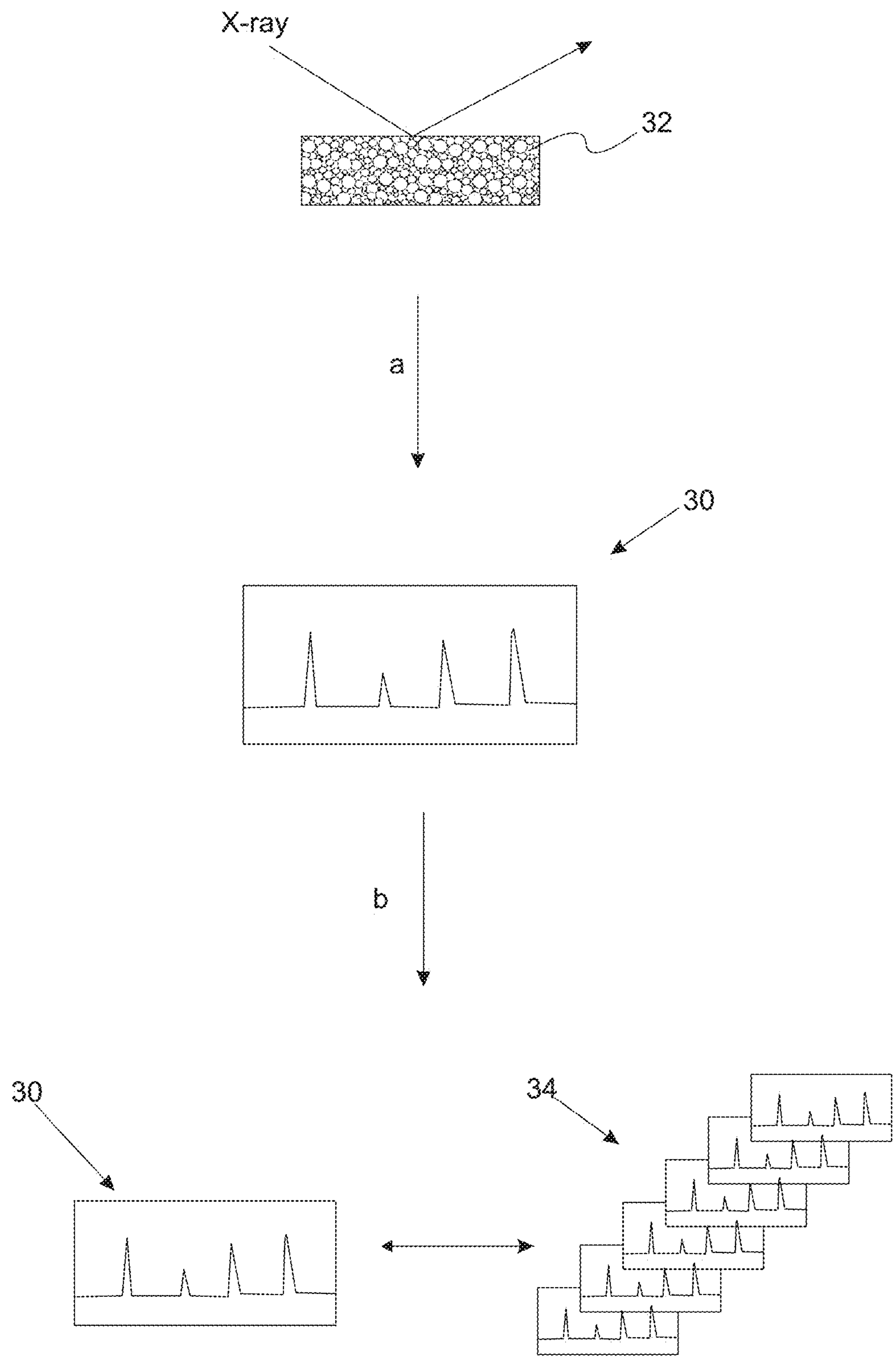
FIG. 2 provides a schematic flowchart showing the determination of the amount of lithium in a lithium-ion battery electrode sample.

With reference to FIG. 2, a schematic illustration of a method for determining an amount of lithium in a lithium-ion battery electrode (i.e., cathode or anode) sample is provided. In step a), powder X-ray diffraction peaks 30 of the lithium-ion battery electrode sample 32 are determined (i.e., measured). In step b), the powder X-ray diffraction peaks 30 of the lithium-ion battery electrode sample 32 are compared with a set 34 of lithium-containing samples having pre-determined lithium concentrations to determine the amount of lithium in the lithium-ion battery electrode sample 32.

Figure 3:
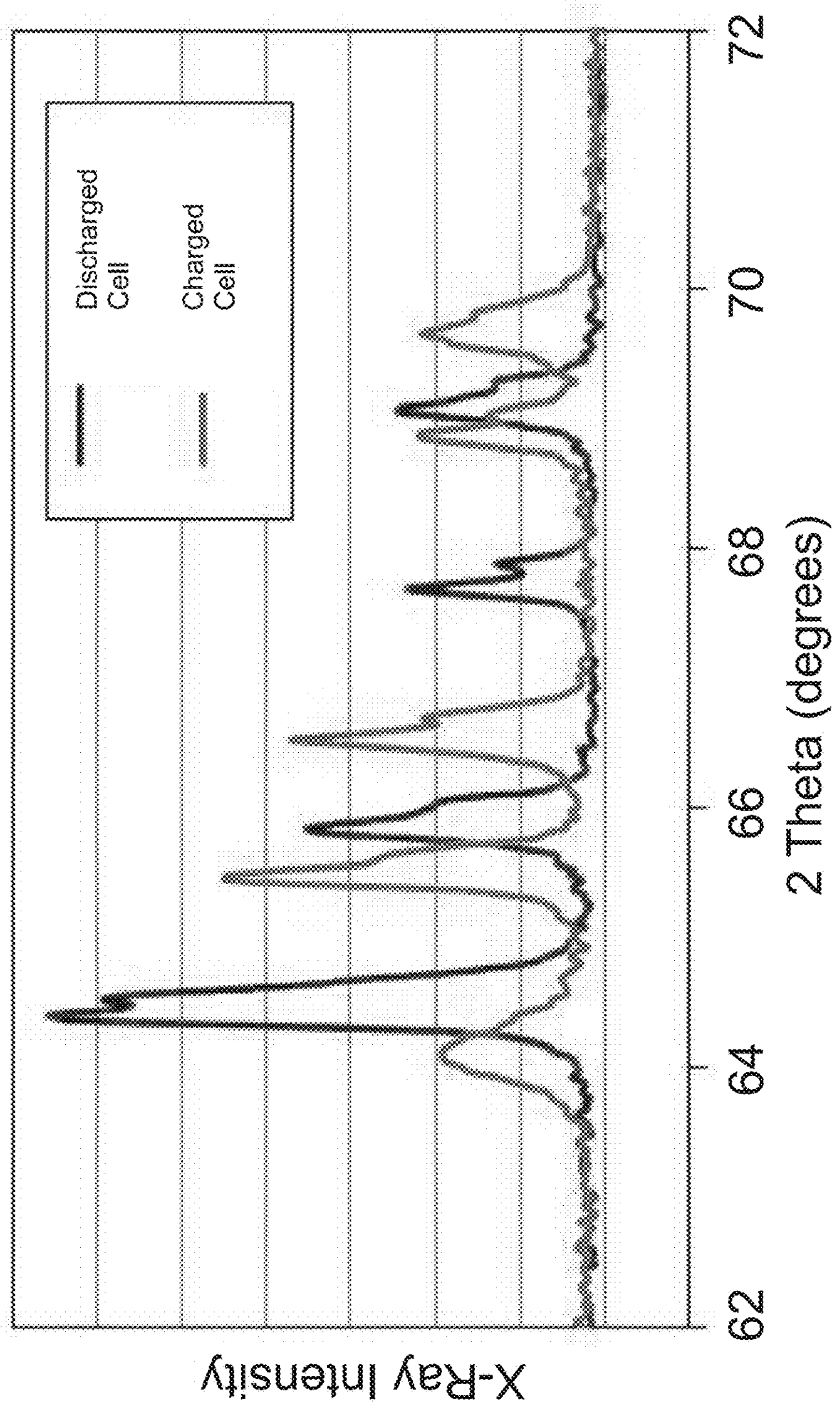
FIG. 3 provides XRD peaks for lithium-ion battery cathode that is fully discharged and fully charged.
Figure 4:
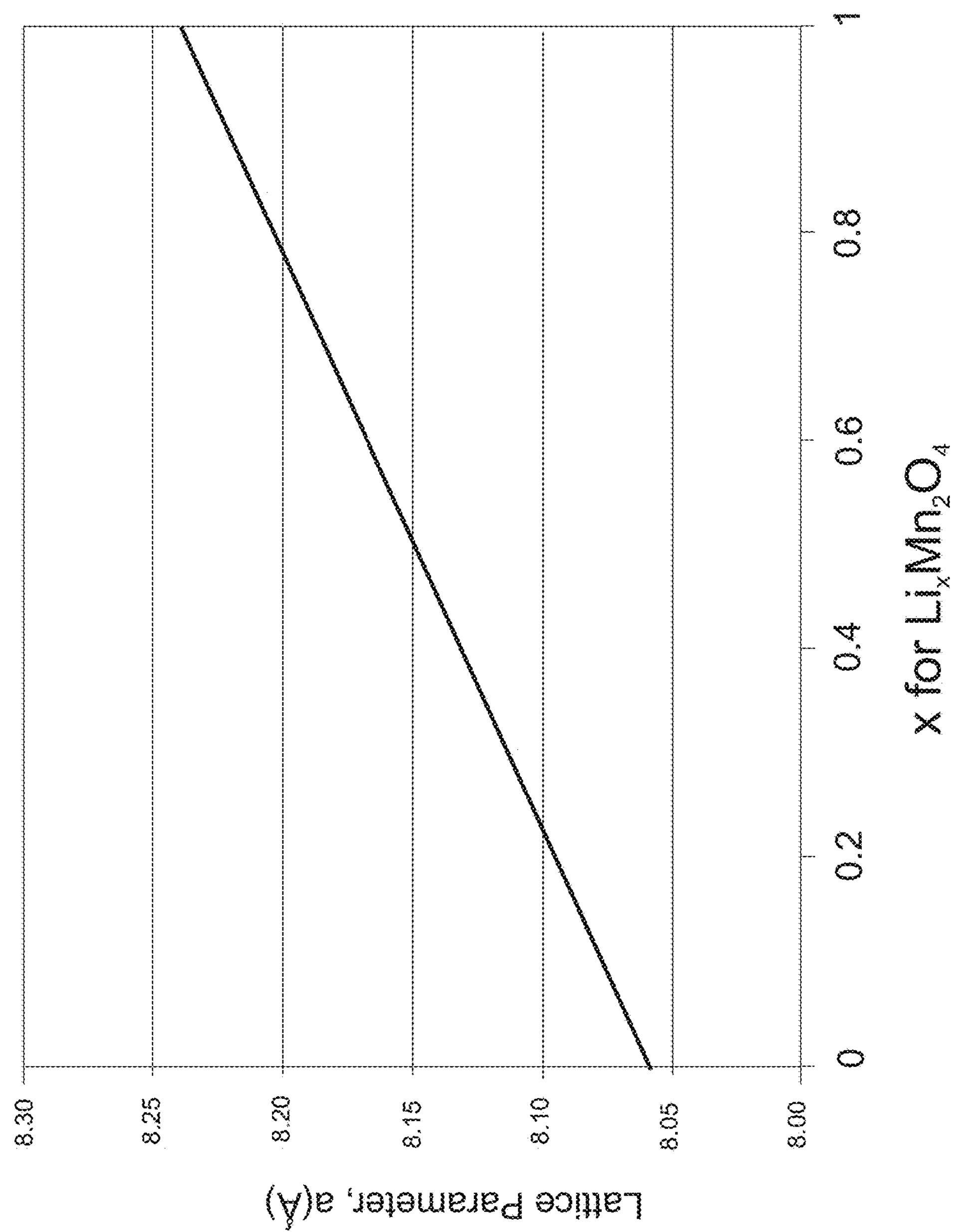
FIG. 4 provides a lithium-ion battery cathode calibration curve for the spinel phase described by formula $Li_xMn_2O_4$.

In one variation, the lithium-ion battery electrode sample 32 is a lithium-ion battery cathode sample. In this variation, a calibration curve is constructed from the set of lithium-containing samples having pre-determined lithium concentrations. The calibration curve allows estimation of (i.e. determination of) the amount of lithium in the lithium-ion battery cathode sample. In a refinement, the X-ray diffraction peaks of the lithium battery cathode include diffraction peaks from a spinel phase, a layered phase, or combinations thereof. FIG. 3 provides X-ray peaks for fully discharged and fully charged cathode material. Typically, the calibration curve provides a plot of at least one lattice parameter for the spinel phase versus lithium concentration for the set of lithium-containing samples having pre-determined lithium concentrations. The lattice parameter for the lithium-ion battery cathode sample is determined from X-ray diffraction peaks to provide calculated lattice parameters. Typically, the lattice parameters are determined by Reitveld refinements of the XRD data. The calculated lattice parameter is compared to the calibration curve to determine the amount of lithium in the lithium-ion battery cathode sample. For example, the spinel phase is described by formula $Li_xMn_2O_4$ where x is from 0 to 1 and the lattice parameter can be an "a" lattice parameter. In the variation depicted in FIG. 4, the calibration curve is estimated as linear defined by the equation $x=(5.53+1-10\%)\cdot a-(44.59+/-10\%)$ as x varies from 0 to x with the "a" lattice parameter varying from about 8.06 angstroms to about 8.24 angstroms In this variation, the calibration curve provides a plot of at least one lattice parameter (e.g., the "a" parameter) for the layered phase versus lithium concentration for the set of lithium-containing samples having pre-determined lithium concentrations. At least one lattice parameter (e.g., the "a" parameter) calculated for the lithium-ion battery electrode sample is compared to the calibration curve to determine the amount of lithium in the lithium-ion battery cathode sample.

Figure 5:
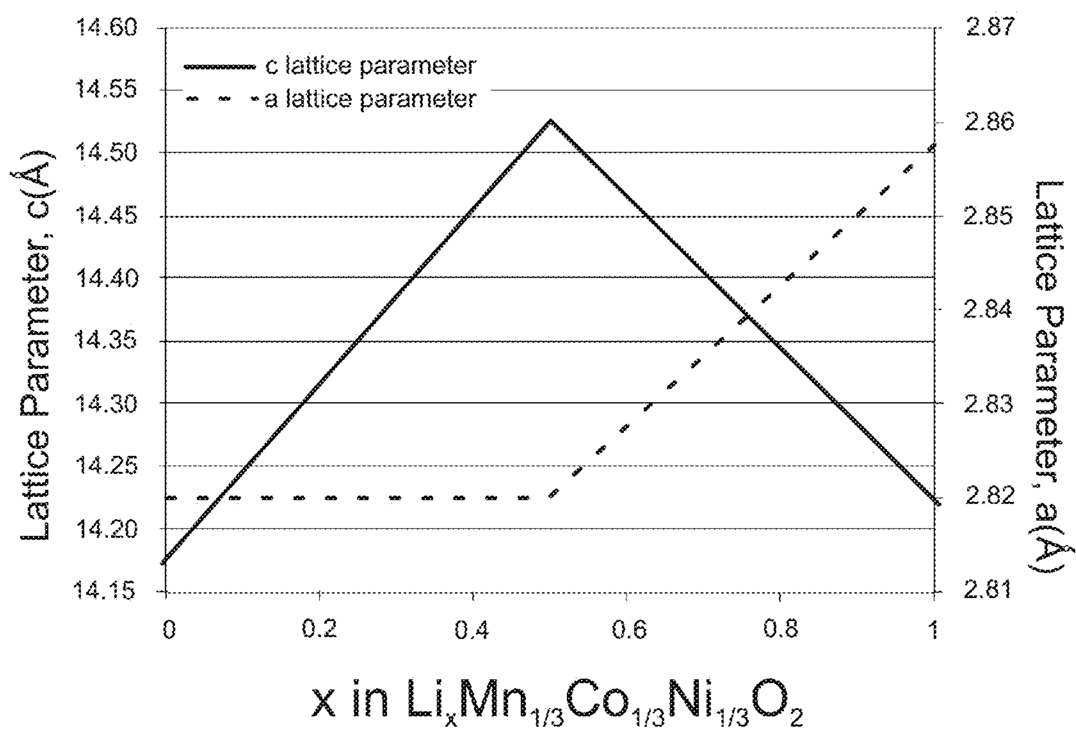
FIG. 5 provides a lithium-ion battery cathode calibration curve for the layered phase described by formula $Li_xMn_{1/3}Co_{1/3}Ni_{1/3}O_2$.

In another refinement, the layered phase is described by formula $Li_xMn_{1/3}CO_{1/3}Ni_{1/3}O_2$ where x is from 0 to 1. In this refinement, the lattice parameters includes an "a" lattice parameter, a "c" lattice parameter and combinations thereof. The lattice parameters for the lithium-ion battery cathode sample are determined from the X-ray diffraction peaks. As depicted in FIG. 5, the calibration curve is linear defined by the equation $x=-(1.65+/-10\%)\cdot c+24.47+/-10\%)$ when a $\geq 2.82$ angstroms as x varies from 0.5 to 1 with the "c" lattice parameter varying from about 14.23 angstroms to about 14.5 angstroms. Moreover, the calibration curve is linear defined by the equation $x=(13.16+/-10\%)\cdot a-(36.61+/-10\%)$ as x varies from 0.5 to 1 with the "a" lattice parameter varying from about 2.82 angstroms to about 2.86 angstroms. The calibration curve is linear defined by the equation $x=(1.41+/-10\%)\cdot c-(19.56+/-10\%)$ when a $\leq 2.82$ angstroms as x varies from 0 to 0.5 with the "c" lattice parameter varying from about 14.17 angstroms to about 14.23 angstroms.

Figure 6:
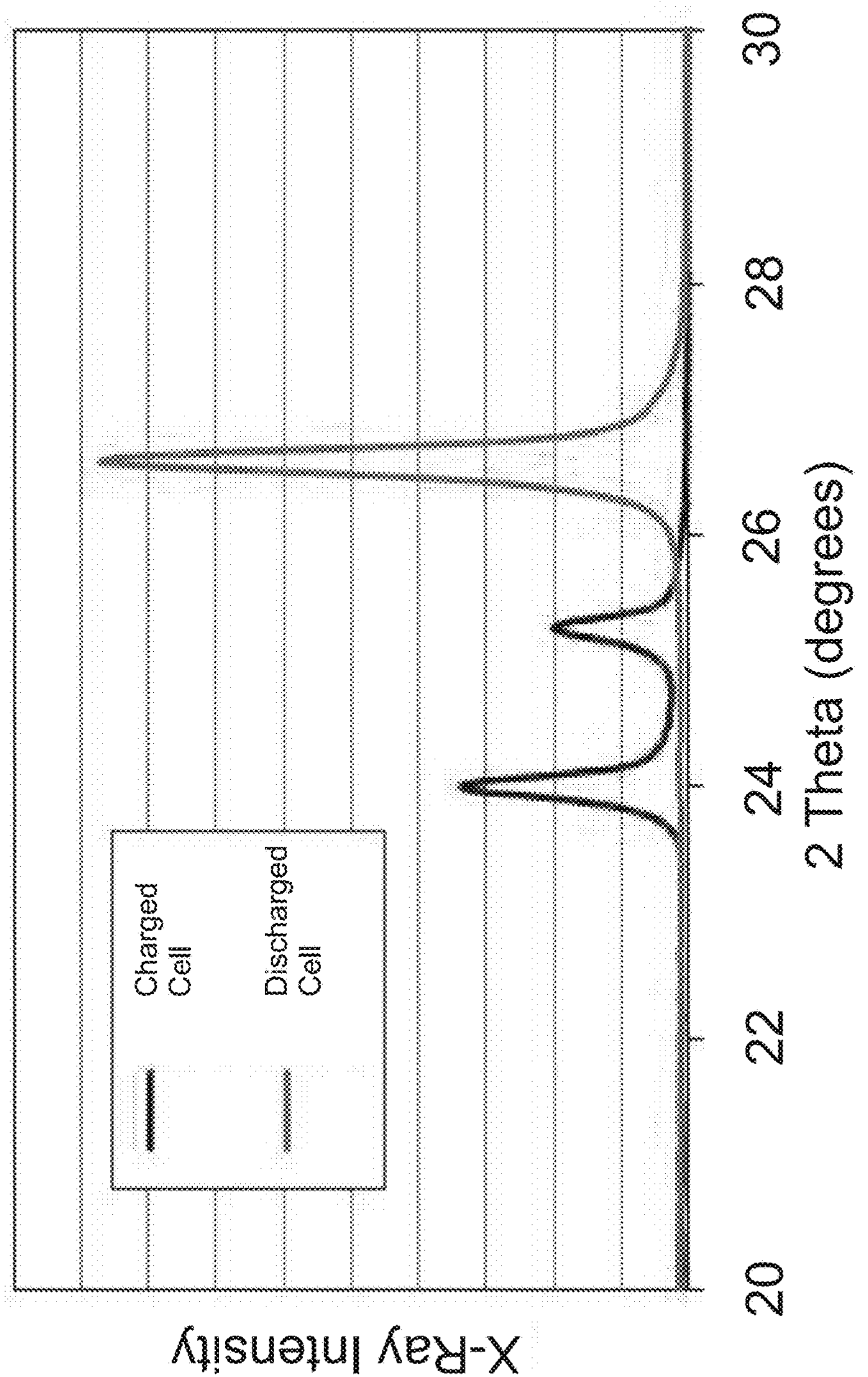
FIG. 6 provides XRD peaks for lithium-ion battery anode that is fully discharged and fully charged.

In another variation, the lithium-ion battery electrode sample is a lithium-ion battery anode sample. In such samples, the X-ray diffraction peaks of the lithium battery anode sample include diffraction peaks from a $LiC_6$, $LiC_{12}$, or combinations thereof. FIG. 6 provides XRD peaks for lithium-ion battery anode that is fully discharged and fully charged. The size of the $LiC_6$ and $LiC_{12}$ diffraction peaks in the lithium-ion anode sample are compared to the size of the $LiC_6$ and $LiC_{12}$ diffraction peaks in set of lithium-containing samples having pre-determined lithium concentrations to determine the amount of lithium in the lithium-ion anode sample. In this regard, the size of diffraction peaks is determined by peak height or by integrated area of the diffraction peaks. Moreover, the percentage of graphite fully intercalated with lithium is defined as $\%\ Li=(2\cdot I_{LiC6}++I_{LiC12})/2\cdot(I_{LiC6}+I_{LiC12}+I_{C6})$ where $I_{LiC6}$ is the peak intensity for the $LiC_6(001)$ diffraction peak, $I_{LiC12}$ is the peak intensity for the $LiC_{12}(002)$ diffraction peak and $I_{C6}$ is the peak intensity for the graphite(002) diffraction peak intensity.

The following examples illustrate the various embodiments of the present invention. Those skilled in the art will recognize many variations that are within the spirit of the present invention and scope of the claims.

Data Analysis

All batteries characterized in this study are lithium-ion batteries (LIBs). The LIBs are pouch cells with a prismatic construction and a nominal beginning of life (BOL) capacity rating of 15 Amp-hours. The batteries employ a mixed "layered" $LiMn_{1/3}Co_{1/3}Ni_{1/3}O_2$ and "spinel" $LiMn_2O_4$ composite cathode, carbon anode and a 1 M LiPF6 in DMC/EMC/EC electrolyte solution. A summary of the history and performance of all batteries characterized can be found in Table 1.

TABLE 1

Cell description, testing history and cell performance data

| Cell Identification | Test History | Capacity@ 1 C, Ah |
|---|---|---|
| Control cell | control battery, not cycled or thermally aged (BOL) | 15.09 |
| Control cell | control battery, not cycled or thermally aged (BOL) | 15.05 |
| Calendar aged cell | 80% initial capacity, 675 days (1.85 Y0 at 45° C. and 80% SOC | 12.2 |
| Cycled cell | 60% initial capacity, 4329 cycles (1.81 Y) at 35° C. | 8.81 |
| cell | 60% initial capacity, 4741 cycles (2.22 Y) at 35° C. | 9.10 |

X-ray diffraction data were collected using a Cu K-alpha radiation (40 kV and 40 mA). The samples were prepared and sealed with a Kapton film in a glove box prior to the XRD analysis.

The cathode samples were scanned using Bragg Brentano geometry also known as coupled theta-two theta. Due to the high absorption of Cu K-alpha radiation by the cathode active materials, the XRD data from the cathode only is representative approximately 10 μm. Anodes and separators were scanned using the parallel beam geometry also known as two-theta scan mode (detector scan); 5° incidence angle. Due to the low absorption of Cu K-alpha radiation by the anode active materials and separator materials, the XRD data from the anode and separator are expected to representative of the complete component. The phases present in each sample were assigned by matching the XRD patterns to reference data in International Centre of Diffraction Data (ICDD) reference database. The lattice parameters were determined by Reitveld refinement.

Data Analysis

XRD data were collected from a fully charged (lithiated) anode and compared to that of a discharged (de-lithiated) anode. As shown in FIG. 5, the discharged anode shows only a graphite diffraction peak at 26.4° two-theta. In contrast, the charged anode shows two lithiated graphite peaks which match reference data for $LiC_6$ and $LiC_{12}$. The Li—C peak found at ~24.0° has more lithium (LiC6) and the Li—C peak found at ~25.3° two-theta has a lower Li content ($LiC_{12}$). Based on the above findings we compared the XRD data from control, calendar aged and cycle aged anodes. The XRD data indicated less than 1% graphite in all of the samples in the aging study to be lithiated.

The XRD data from the cathode samples identified two crystalline phases: a spinel phase; $Li_xMn_2O_4$ and layered phase; $Li_xMn_{1/3}Co_{1/3}Ni_{1/3}O_2$. The XRD peak widths were in the control and aged cathodes indicating no significant fragmentation of the cathode active materials. However, some variation in peak positions was observed. Therefore data were collected from a full discharged cell and fully charged cell. As shown in FIG. 3, the diffraction peaks shift is related to the degree of lithiation and is directly attributable to changes in the crystal structure lattice parameter(s).

Figure 7:
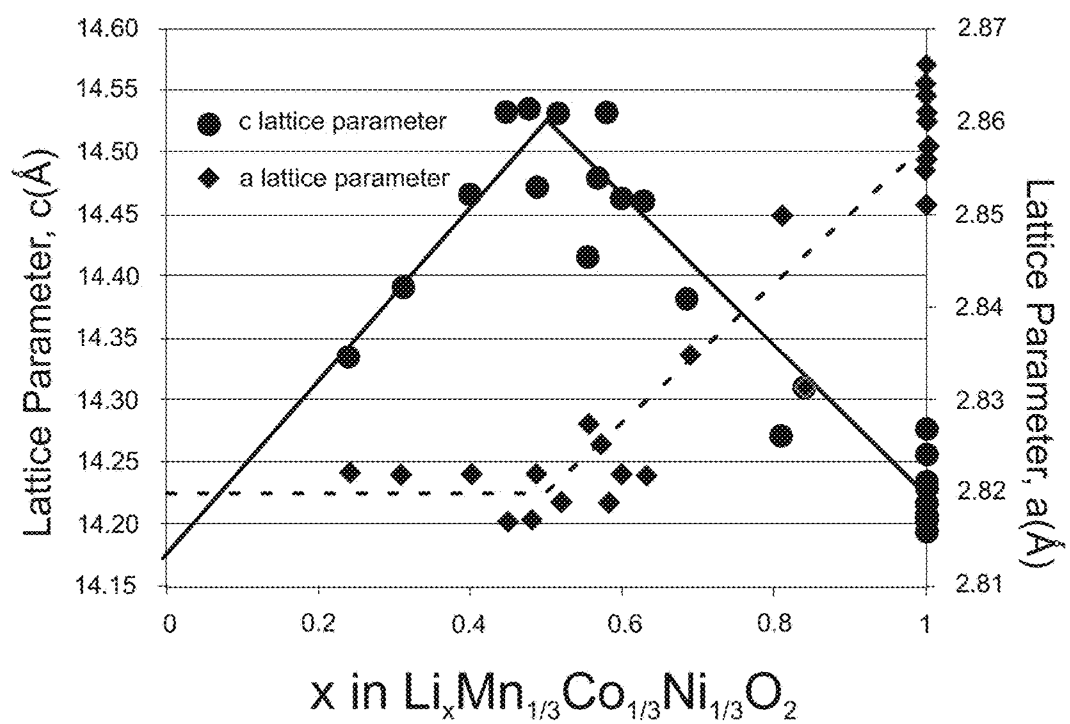
FIG. 7 plots the lattice parameters of the reference data as a function of Li stoichiometry for the layered phase.
Figure 8:
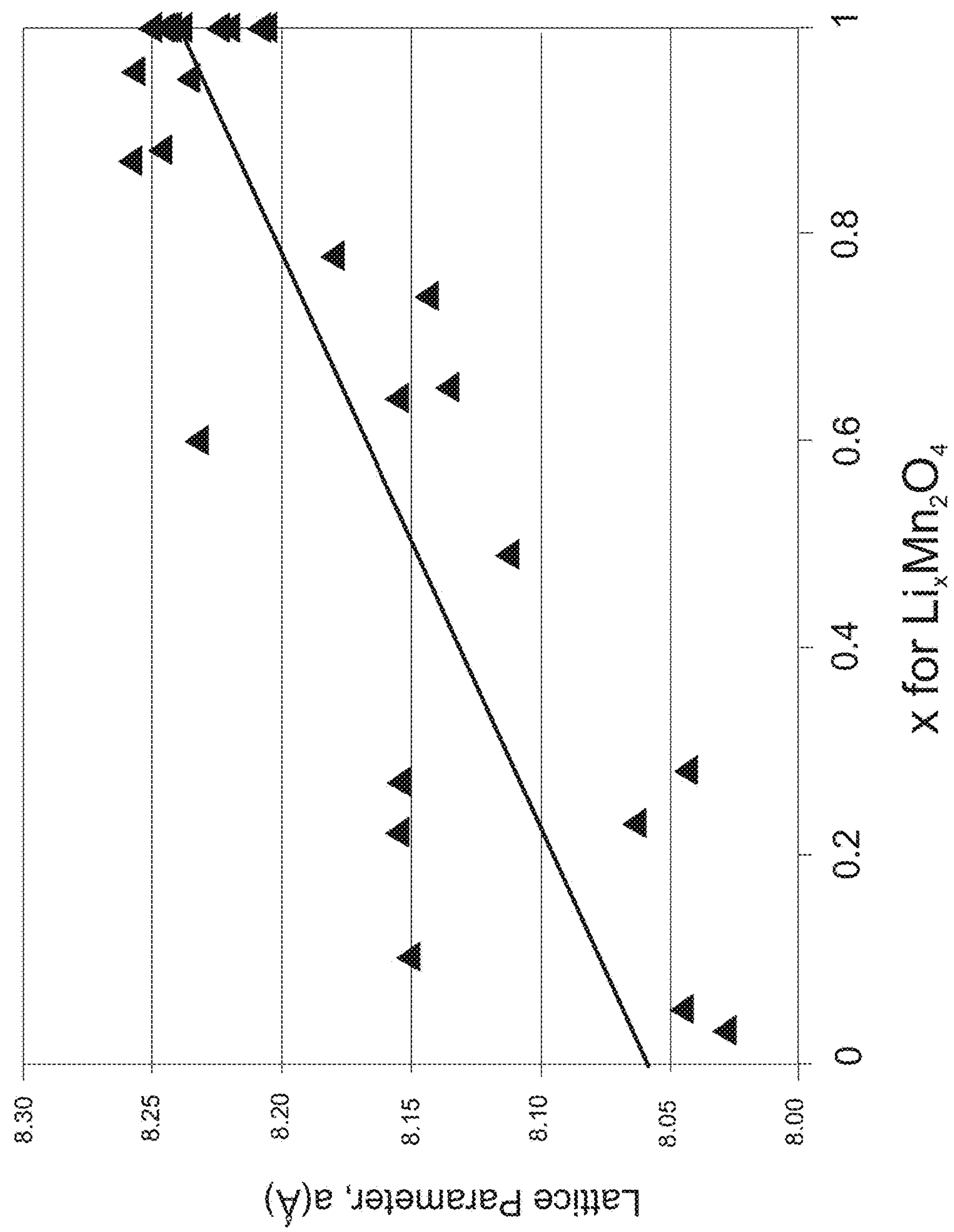
FIG. 8 plots the lattice parameters of the reference data as a function of Li stoichiometry for the spinel phase.

Reitveld refinements of the XRD data were performed to determine the lattice parameters and relative weight fractions of the spinel and layered phases. To quantify the lithiation in the cathode active materials, the calculated lattice parameters were compared to reference data from ICDD. FIG. 7 plots the lattice parameters of the reference data as a function of Li stoichiometry for the layered phase. From the diagram, the 'a' lattice parameter is constant from Li=0 to Li=0.5 but the 'c' lattice parameter increases linearly with increasing Li concentrate. At Li concentrations 0.5-1.0, the 'a' lattice parameter increases linearly with increasing Li concentration but the 'c' lattice parameter decreases linearly with increasing Li concentrate. FIG. 8 plots the lattice parameters of the reference data as a function of Li stoichiometry for the spinel phase. For the spinel phase, the lattice parameter increases linearly with increasing Li concentration.

The degree of lithiation reported in Tables 2 and 3 was then calculated by comparing the measured lattice parameters to those in FIGS. 7 and 8. In the layered material, Li cycles between 0.8 and 0.5 and in the spinel material Li cycles between 0.1 and 0.8; Tables 2 and 3, respectively. During aging Li concentration is reduced in the layered structure but remains relatively unchanged for the spinel phase.

TABLE 3

Lattice parameter, estimated lithiation and weight fraction of the layered structure; $Li_xMn_{1/3}Ni_{1/3}O_2$

| CELL | a (Å) | c (Å) | Cell Volume (Å$^3$) | $Li_x$, X = | Wt %* |
|---|---|---|---|---|---|
| Control Cell | 2.8436 Å | 14.3227 Å | 115.5 | 0.8 | 62% |
| Control Cell | 2.8406 Å | 14.3378 Å | 115.6 | 0.8 | 64% |
| Calendar Aged Cell | 2.8338 Å | 14.4066 Å | 115.3 | 0.7 | 64% |
| Cycled Aged Cell | 2.8238 Å | 14.4837 Å | 115.1 | 0.6 | 72% |
| Cycled Aged Cell | 2.8289 Å | 14.4549 Å | 115.0 | 0.6 | 73% |
| Charged Cell | 2.8170 Å | 14.5163 Å | 115.4 | 0.5 | 72% |

TABLE 3

Lattice parameter, estimated lithiation and weight fraction of the spinel structure; $Li_xMn_2O_2$

| CELL | a (Å) | Cell Volume (Å$^3$) | $Li_x$, X = | Wt %* |
|---|---|---|---|---|
| Control Cell P4J | 8.2057 Å | 552.5 | 0.8 | 38% |
| Control Cell P 4N | 8.2040 Å | 552.2 | 0.8 | 36% |
| Calendar Aged Cell P4E | 8.2072 Å | 552.8 | 0.8 | 36% |
| Cycled Aged Cell LP8 | 8.2015 Å | 551.7 | 0.8 | 27% |
| Cycled Aged Cell P4G | 8.2096 Å | 553.3 | 0.8 | 27% |
| Charged Cell | 8.0813 Å | 527.8 | 0.1 | 28% |

The relative weight fractions of the spinel and layered phases reported in Tables 2 and 2 differ from the nominal value of 50 wt %. This difference is due to the surface of the cathodes being enriched in the layered phase and the limited penetration depth of the Cu kα radiation in Mn and Co materials. This segregation occurs because of the particle size difference of the two active materials. In the cathodes, the layered phase particles are smaller than the spinel phase particles. Thus when the electrodes are coated, the smaller layered phase particles are more liable to fill the voids created at the surface of the electrode and current collector interface. Since Mn and Co have a high mass absorption coefficients for Cu kα radiation, the XRD sampling depth is limited to approximately 10 μm in the cathode and consequently the XRD data is not necessary indicative of the bulk composition.

Also noteworthy from Table 2 is that the apparent weight fraction of the layered phase as determined from the Reitveld refinements increases with loss of lithium. This anomaly is suspected to be an artifact of the refinement and is attributed to not refining atomic positions and occupancies in the crystal structure.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for determining an amount of lithium in a lithium-ion battery electrode sample, the method comprising:

determining powder X-ray diffraction peaks of the lithium-ion battery electrode sample; and comparing the powder X-ray diffraction peaks of the lithium-ion battery electrode sample with a set of lithium-containing samples having pre-determined lithium concentrations to determine the amount of lithium in the lithium-ion battery electrode sample wherein the lithium-ion battery electrode sample is a lithium-ion battery cathode sample such that X-ray diffraction peaks of the lithium-ion battery cathode sample include diffraction peaks from a spinel phase, a layered phase, or combinations thereof and wherein a calibration curve is constructed from the set of lithium-containing samples having pre-determined lithium concentrations, the calibration curve allowing determination of the amount of lithium in the lithium-ion battery cathode sample, the calibration curve providing a plot of at least one lattice parameter for the spinel phase versus lithium concentration for the set of lithium-containing samples having pre-determined lithium concentrations.

2. The method of claim 1 further comprising determining at least one lattice parameter for the lithium-ion battery electrode sample that is compared to the calibration curve to determine the amount of lithium in the lithium-ion battery cathode sample.

3. The method of claim 2 wherein the at least one lattice parameter is an "a" lattice parameter.

4. The method of claim 3 wherein the spinel phase is described by formula $Li_xMn_2O_4$ where x is from 0 to 1.

5. The method of claim 3 wherein the calibration curve is linear as x varies from 0 to x with the "a" lattice parameter varying from about 8.06 angstroms to about 8.24 angstroms.

6. The method of claim 1 further comprising determining powder X-ray diffraction peaks of a lithium-ion battery anode sample; and comparing the powder X-ray diffraction peaks of the lithium-ion battery anode sample with a set of lithium-containing samples having pre-determined lithium concentrations to determine the amount of lithium in the lithium-ion battery anode sample.

7. The method of claim 6 wherein the X-ray diffraction peaks of the lithium-ion battery anode sample include diffraction peaks from $LiC_6$, $LiC_{12}$, graphite or combinations thereof.

8. The method of claim 7 wherein the size of the $LiC_6$, $LiC_{12}$, and graphite diffraction peaks in the lithium-ion battery anode sample are compared to the size of the $LiC_6$, $LiC_{12}$, and graphite diffraction peaks in the set of lithium-containing samples having pre-determined lithium concentrations to determine the amount of lithium in the lithium-ion battery anode sample.

9. The method of claim 8 wherein size of diffraction peaks is determined by peak height or by integrated area of the diffraction peaks.

10. A method for determining an amount of lithium in a lithium-ion battery electrode sample, the method comprising:

determining powder X-ray diffraction peaks of the lithium-ion battery electrode sample; and comparing the powder X-ray diffraction peaks of the lithium-ion battery electrode sample with a set of lithium-containing samples having pre-determined lithium concentrations to determine the amount of lithium in the lithium-ion battery electrode sample wherein the lithium-ion battery electrode sample is a lithium-ion battery cathode sample such that X-ray diffraction peaks of the lithium-ion battery cathode sample include diffraction peaks from a spinel phase, a layered phase, or combinations thereof and wherein a calibration curve is constructed from the set of lithium-containing samples having pre-determined lithium concentrations, the calibration curve allowing determination of the amount of lithium in the lithium-ion battery cathode sample, the calibration curve providing a plot of at least one lattice parameter for the layered phase versus lithium concentration for the set of lithium-containing samples having pre-determined lithium concentrations.

11. The method of claim 10 further comprising determining at least one lattice parameter for the lithium-ion battery electrode sample that is compared to the calibration curve to determine the amount of lithium in the lithium-ion battery cathode sample.

12. The method of claim 11 wherein the at least one lattice parameter includes an "a" lattice parameter, a "c" lattice parameter and combinations thereof.

13. The method of claim 12 wherein the layered phase is described by formula $Li_xMn_{1/3}Co_{1/3}Ni_{1/3}O_2$ where x is from 0 to 1.

14. The method of claim 13 wherein the calibration curve is linear as x varies from 0.5 to 1 with the "c" lattice parameter varying from about 14.23 angstroms to about 14.5 angstroms.

15. The method of claim 13 wherein the calibration curve is linear as x varies from 0.5 to 1 with the "a" lattice parameter varying from about 2.82 angstroms to about 2.86 angstroms.

16. The method of claim 13 wherein the calibration curve is linear as x varies from 0 to 0.5 with the "c" lattice parameter varying from about 14.17 angstroms to about 14.23 angstroms.

* * * * *